US008512940B2

(12) United States Patent
Koshiba et al.

(10) Patent No.: US 8,512,940 B2
(45) Date of Patent: Aug. 20, 2013

(54) METHOD FOR PRESERVING LIVER IN A SOLUTION COMPRISING DIBUTYRYL CAMP

(75) Inventors: Takaaki Koshiba, Kyoto (JP); Xiangdong Zhao, Kyoto (JP); Hiromi Wada, Kyoto (JP); Takayuki Nakamura, Kyoto (JP); Masami Nakamura, legal representative, Kyoto (JP); Koichi Tanaka, Kyoto (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 13/222,407

(22) Filed: Aug. 31, 2011

(65) Prior Publication Data

US 2011/0311959 A1    Dec. 22, 2011

Related U.S. Application Data

(63) Continuation of application No. 12/083,503, filed as application No. PCT/JP2006/320796 on Oct. 12, 2006, now abandoned.

(30) Foreign Application Priority Data

Oct. 13, 2005    (JP) ................................. 2005-299314

(51) Int. Cl.
*A01N 1/00*    (2006.01)
(52) U.S. Cl.
USPC .......................................................... 435/1.2

(58) Field of Classification Search
None
See application file for complete search history.

(56) References Cited

FOREIGN PATENT DOCUMENTS

EP    0 580 444    *    7/1993

OTHER PUBLICATIONS

Van Ness et al., "Dibutyryl cAMP Reduces Nonparenchymal Cell Damageduring Cold Preservation of Rat Livers", Journal of Surgical Research 58 : 728-731 (1995).*
Canadian Office Action issued Feb. 10, 2010 in corresponding Canadian Patent Application No. 2,625,628.
Chen, Fengshi, *"Development of New Organ Preservation Solutions in Kyoto University"*, Yonsei Medical Journal, 2004, vol.45, No. 6, pp. 1107-1114.
Nakamura et al., "Dibutyryl cyclic adenosine monophosphate attenuates lung injury caused by cold preservation and ischemia-reperfusion", J. Thoracic Cardiovascular Surgery 114: 635-642 (1997).
Certificate of Web Release by Professor Ph. Morel and the website of 12th Congress of the European Society for Organ Transplantation (ESOT) 2005's program attached to the Certificate, Oct. 13, 2005.

* cited by examiner

*Primary Examiner* — Sandra Saucier
(74) *Attorney, Agent, or Firm* — Wenderoth, Lind & Ponack, L.L.P.

(57) ABSTRACT

The present invention provides a liver preservation solution containing trehalose and dibutyryl-cAMP. The content of nitroglycerin in the preservation solution is preferably lower than 0.44 mM. In the liver preservation solution of the present invention, since the toxicity due to nitroglycerin, which is observed during liver preservation, has been improved, liver transplantation can be performed with a high engrafted rate.

2 Claims, 4 Drawing Sheets

METHOD FOR PRESERVING LIVER IN A SOLUTION COMPRISING DIBUTYRYL CAMP

This application is a continuation of application Ser. No. 12/083,503, filed May 21, 2009 now abandoned, which is the National Stage of International Application No. PCT/JP2006/320796, filed Oct. 12, 2006.

TECHNICAL FIELD

The present invention relates to a liver preservation solution, wherein the toxicity due to nitroglycerin is improved.

BACKGROUND ART

At present, University of Wisconsin solution (UW solution) is generally used for brain death liver m transplantation in the US and Europe (Transplant proc, vol. 31, p. 2069-2070, 1999). This is because UW solution enables a longer-term cold ischemic preservation of the liver as compared to other organ preservation solutions. However, since UW solution is extremely highly viscous, the blood in blood vessels needs to be washed away with Ringer's solution etc. having low viscosity, prior to the start of the cold ischemic preservation of the liver. In addition, perfusion with UW solution is time-consuming. Further, UW solution is an intracellular preservation solution (electrolyte is equivalent to intracellular composition) and has a high potassium concentration (125 mM). A high potassium concentration causes contraction of blood vessels, causing long time organ perfusion. What is more, UW solution in the liver needs to be once substituted with Ringer's solution etc. immediately before recanalizing the blood flow after transplantation of the liver into a patient, so that high concentration potassium will not flow into the body of the patient. Moreover, since UW solution contains a chemically-unstable active oxygen scavenger (radical scavenger) as a component, the shelf life thereof is short even when preserved in a cold place, and the unit price is very high.

To solve these disadvantages, the present inventors have developed ET-Kyoto solution and New ET-Kyoto solution, which are extracellular solutions having a completely different composition from that of UW solution and a low potassium concentration, and containing trehalose which is a saccharide that stabilizes cellular membrane and suppresses cell injury (JP-B-3253131, Yonsei Medical Journal, vol. 45, No. 6, p. 1107-1114, 2004). New ET-Kyoto solution has a composition similar to that of ET-Kyoto solution, but is different from ET-Kyoto solution in that it contains dibutyryl cAMP (db-cAMP), nitroglycerin and N-acetylcysteine. It is described that addition of db-cAMP and nitroglycerin to a preservation solution further enhances post-transplant organ function as compared to ET-Kyoto solution (Yonsei Medical Journal, vol. 45, No. 6, p. 1107-1114, 2004).

It has already been demonstrated at the animal experiment level that ET-Kyoto solution exhibits an effect equivalent to that of UW solution used for cold ischemic preservation of the kidney, lung, muscle or skin. However, no detailed report has documented as to the effect on the liver preservation.

In the lung preservation, the New ET-Kyoto solution shows an effect superior to that of UW solution, and has already been introduced into the clinical application and lung transplantation in Kyoto University.

Thus, the development of a liver preservation solution, which is more superior in an action to maintain organ function, and superior in safety, operability and chemical stability, has been desired.

In view of the above-mentioned situation, it is an object of the present invention to provide a liver preservation solution, which is superior in an action to maintain organ function, as well as safety, easiness of use and chemical stability.

DISCLOSURE OF THE INVENTION

The present inventors have conducted intensive studies in an attempt to achieve the aforementioned object.

As a result, they have found a problem in that when the liver preserved in a New ET-Kyoto solution confirmed to show a superior effect for the preservation of a lung graft and the like is transplanted to a recipient animal without perfusion with Ringer's solution etc. in the same manner as for lung transplantation, unexpected toxicity absent in a recipient animal for lung transplantation is observed, which decreases the survival rate of the animal after transplantation. Thus, they have further investigated the cause of the toxicity and found that nitroglycerin contained in the New ET-Kyoto solution causes the toxicity, and that the toxicity can be reduced by lowering the content of nitroglycerin to a level below a certain value. Furthermore, they have found that addition of dibutyryl cAMP to an ET-Kyoto solution strikingly improves the survival rate (engrafted rate) after liver transplantation under the conditions where the toxicity of nitroglycerin is not expressed, and that the effect of dibutyryl cAMP addition is specific to the ET-Kyoto solution, which resulted in the completion of the present invention.

Accordingly, the present invention relates to the following.

[1] A liver preservation solution comprising trehalose and dibutyryl cAMP.
[2] The preservation solution of [1], having a nitroglycerin content of lower than 0.44 mM.
[3] The preservation solution of [1], having a nitroglycerin content of not more than 0.0044 mM.
[4] The preservation solution of [1], which is substantially free of nitroglycerin.
[5] The preservation solution of [1], wherein the concentration of dibutyryl cAMP is within the range of 0.005-10 mM.
[6] The preservation solution of [1], wherein the concentration of trehalose is within the range of 50-240 mM.
[7] The preservation solution of [1], further comprising hydroxyethylstarch.
[8] The preservation solution of [1], further comprising at least the following components within the following range:

| | |
|---|---|
| Na$^+$ | 10-140 mM |
| K$^+$ | 4-140 mM |
| H$_2$PO$_4^-$ or HPO$_4^{--}$ | 12-65 mM |
| at least one kind selected from Cl$^-$, HCO$_3^-$, CO$_3^{--}$, organic acid and organic acid anion | 15-150 mM. |

[9] A liver preservation solution comprising at least the following components within the following range:

| | |
|---|---|
| dibutyryl cAMP | 0.005-10 mM |
| trehalose | 50-240 mM |
| hydroxyethylstarch | 1-80 g/l |
| Na$^+$ | 10-140 mM |
| K$^+$ | 4-140 mM |

-continued

| | |
|---|---|
| H₂PO₄⁻ or HPO₄⁻⁻ | 12-65 mM |
| at least one kind selected from Cl⁻, HCO₃⁻, CO₃⁻⁻, organic acid and organic acid anion | 15-150 mM. |

[10] The preservation solution of [9], having a nitroglycerin content of lower than 0.44 mM.

[11] A kidney preservation solution comprising trehalose and dibutyryl cAMP.

The liver preservation solution of the present invention has the following advantages.

(1) In the liver preservation solution of the present invention, the toxicity due to nitroglycerin, which occurs during preservation of the liver in New ET-Kyoto solution, has been improved. Further, the liver preservation solution of the present invention has a potassium concentration lower than that of UW solution. Accordingly, the blood can be reperfused after preservation without substitution of the preservation solution in the liver with Ringer's solution and the like.

(2) Since the liver preservation solution of the present invention has low viscosity, the initial perfusion with Ringer's solution and the like is not necessary when the liver cold ischemia is started.

(3) Since the liver preservation solution of the present invention has low viscosity and low potassium concentration, the perfusion time is short when the liver cold ischemia is started.

(4) The liver preservation solution of the present invention has a chemically stable composition and can be stored at room temperature for a long time.

(5) The liver preservation solution of the present invention has low unit price.

(6) The preservation solution has clearly superior liver preservation capability as compared to existing organ preservation solution such as UW solution and the like.

BEST MODE FOR CARRYING OUT THE INVENTION

Figure 1:
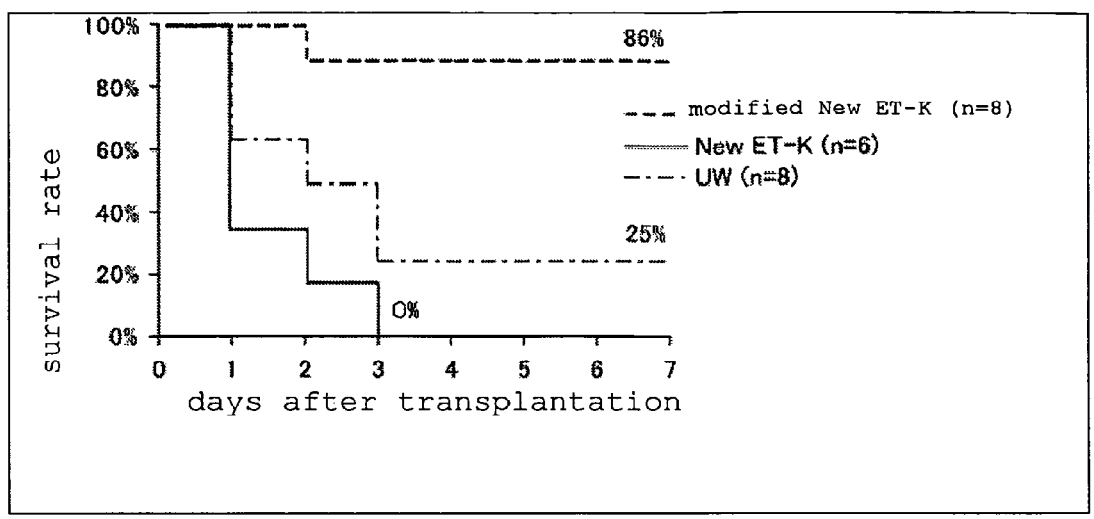
FIG. 1 is a graph showing 7-day survival rate after liver transplantation.

The present invention provides a liver preservation solution containing trehalose and dibutyryl cAMP.

Trehalose to be used for the preservation solution of the present invention includes 3 kinds of α,α-trehalose, α,β-trehalose and β,β-trehalose, and naturally-occurring α,α-trehalose is preferably used. While the range of the content of trehalose in the preservation solution of the present invention is not particularly limited as long as the liver function maintaining action of the preservation solution of the present invention is not impaired, it is, for example, 50-240 mM, preferably 100-210 mM, more preferably 100-140 mM, still more preferably 110-130 mM (e.g., 120 mM).

While the range of the content of dibutyryl cAMP in the preservation solution of the present invention is not particularly limited as long as the liver function maintaining action of the preservation solution of the present invention is not impaired, it is, for example, 0.005-10 mM, preferably 0.05-5 mM, more preferably 0.5-4 mM, still more preferably 1.5-3 mM (e.g., 2 mM). Since the preservation solution of the present invention contains dibutyryl cAMP, survival rate (engrafted rate) after liver transplantation is strikingly improved.

The nitroglycerin content of the preservation solution of the present invention is preferably below 0.44 mM. In consideration of the toxicity due to nitroglycerin, a lower nitroglycerin content is more preferable and, for example, it is not more than 0.4 mM, preferably not more than 0.3 mM, more preferably not more than 0.2 mM, still more preferably not more than 0.1 mM (e.g., substantially 0 mM (substantially not containing nitroglycerin)). Particularly, a nitroglycerin content of not more than 0.0044 mM is preferable since toxicity due to nitroglycerin is hardly expressed and the survival rate of the recipient after liver transplantation increases.

The preservation solution of the present invention may contain hydroxyethylstarch (hereinafter also referred to as "HES") to control osmotic pressure of the preservation solution. Hydroxyethylstarch having a degree of substitution within the range of 0.4-0.8 and an average molecular weight of 200000-900000, more preferably 350000-800000, is preferable. While the content of hydroxyethylstarch is not particularly limited as long as the liver function maintaining action of the preservation solution of the present invention is not impaired, it is, for example, 1-80 g/l, preferably 20-40 g/l, more preferably 25-35 g/l (e.g., 30 g/l).

The preservation solution of the present invention may contain various electrolytes to control osmotic pressure and pH of the preservation solution. Examples of the electrolyte include sodium salt or potassium salt of organic acid, sodium chloride, potassium chloride, magnesium chloride, calcium chloride, sodium dihydrogen phosphate, potassium dihydrogen phosphate, disodium hydrogen phosphate, dipotassium hydrogen phosphate, sodium hydrogen carbonate, potassium hydrogen carbonate, sodium carbonate and potassium carbonate. Examples of the organic acid include gluconic acid, lactic acid, acetic acid, propionic acid, β-hydroxybutyric acid and citric acid and the like.

The preservation solution of the present invention preferably further contains at least the following components as electrolytes, preferably within the following range.

Na$^+$ is generally contained at 10-140 mM, preferably 20-120 mM, more preferably 90-110 mM (e.g., 100 mM).

K$^{30}$ is generally contained at 4-140 mM, preferably 20-130 mM, more preferably 40-50 mM (e.g., 44 mM).

H$_2$PO$_4^-$ or HPO$_4^{--}$ is generally contained at 12-65 mM, preferably 20-60 mM, more preferably 20-30 mM (e.g., 25 mM).

At least one kind selected from Cl$^-$, HCO$_3^-$, CO$_3^{--}$, organic acid and organic acid anion is generally contained at 15-150 mM, preferably 20-120 mM, more preferably 90-110 mM (e.g., 100 mM).

A combination of preferable concentration ranges of the electrolytes which can be contained in the preservation solution of the present invention is as follows:

| | |
|---|---|
| Na$^+$ | 10-140 mM |
| K$^+$ | 4-140 mM |
| H$_2$PO$_4^-$ or HPO$_4^{--}$ | 12-65 mM |
| at least one kind selected from Cl$^-$, HCO$_3^-$, CO$_3^{--}$, organic acid and organic acid anion | 15-150 mM |

A combination of more preferable concentration ranges of the electrolytes which can be contained in the preservation solution of the present invention is as follows:

| | |
|---|---|
| Na$^+$ | 20-120 mM |
| K$^+$ | 20-130 mM |
| H$_2$PO$_4^-$ or HPO$_4^{--}$ | 20-60 mM |
| at least one kind selected from Cl$^-$, HCO$_3^-$, CO$_3^{--}$, organic acid and organic acid anion | 20-120 mM |

A combination of still more preferable concentration ranges of the electrolytes which can be contained in the preservation solution of the present invention is as follows:

| | |
|---|---|
| Na$^+$ | 90-110 mM (e.g., 100 mM) |
| K$^+$ | 40-50 mM (e.g., 44 mM) |
| H$_2$PO$_4^-$ or HPO$_4^{--}$ | 20-30 mM (e.g., 25 mM) |
| at least one kind selected from Cl$^-$, HCO$_3^-$, CO$_3^{--}$, organic acid and organic acid anion | 90-110 mM (e.g., 100 mM) |

To prevent swelling or shrinking of cell or tissue during preservation in the preservation solution of the present invention, the osmotic pressure is preferably within the range of 270-450 mOsm/l, more preferably within the range of 270-380 mOsm/l. To prevent acidic decomposition of cell, the pH is preferably within the range of 7-8.

A preferable composition of the preservation solution of the present invention is as follows:

| | |
|---|---|
| dibutyryl cAMP | 0.005-10 mM |
| trehalose | 50-240 mM |
| hydroxyethylstarch | 1-80 g/l |
| Na$^+$ | 10-140 mM |
| K$^+$ | 4-140 mM |
| H$_2$PO$_4^-$ or HPO$_4^{--}$ | 12-65 mM |
| at least one kind selected from Cl$^-$, HCO$_3^-$, CO$_3^{--}$, organic acid and organic acid anion | 15-150 mM |

A more preferable composition of the preservation solution of the present invention is as follows:

| | |
|---|---|
| dibutyryl cAMP | 0.05-5 mM |
| trehalose | 100-210 mM |
| hydroxyethylstarch | 20-40 g/l |
| Na$^+$ | 20-120 mM |
| K$^+$ | 20-130 mM |
| H$_2$PO$_4^-$ or HPO$_4^{--}$ | 20-60 mM |
| at least one kind selected from Cl$^-$, HCO$_3^-$, CO$_3^{--}$, organic acid and organic acid anion | 20-120 mM |

A still more preferable composition of the preservation solution of the present invention is as follows:

| | |
|---|---|
| dibutyryl cAMP | 1.5-3 mM (e.g., 2 mM) |
| trehalose | 110-130 mM (e.g., 120 mM) |
| hydroxyethylstarch | 25-35 g/l (e.g., 30 g/l) |
| Na$^+$ | 90-110 mM (e.g., 100 mM) |
| K$^+$ | 40-50 mM (e.g., 44 mM) |
| H$_2$PO$_4^-$ or HPO$_4^{--}$ | 20-30 mM (e.g., 25 mM) |
| at least one kind selected from Cl$^-$, HCO$_3^-$, CO$_3^{--}$, organic acid and organic acid anion | 90-110 mM (e.g., 100 mM) |

The preservation solution of the present invention can contain, for example, Mg$^{++}$ and/or Ca$^{++}$ within the range of 1-10 mM, besides the above-mentioned components. Moreover, the preservation solution of the present invention can contain other additives, for example, active oxygen scavenger such as N-acetylcysteine and the like, cell activator such as ATP and the like, antibiotic and the like.

The preservation solution of the present invention can be produced easily according to a production method of a transfusion known per se.

While the method of use of the preservation solution of the present invention is not particularly limited, for example, the blood in a liver tissue isolated from a living organism is substituted with the preservation solution of the present invention, and the liver tissue is immersed in the preservation solution of the present invention and directly preserved at a low temperature (e.g., 0-10° C., preferably 1-6° C.).

While the present invention is explained in more detail in the following by referring to Examples, the present invention is not limited in any way by the Examples shown below.

EXAMPLES

Example 1

[1] Materials and Method
(Animal)

Eight-week-old inbred male Lewis rat (SLC) was housed in a chip-bedded cage at room temperature under a 12 hr light/dark cycle and given free access to a standard chow diet and water before operation.

(Preservation Solution)

In 800 ml of distilled water at about 50° C. were dissolved α,α-trehalose (41 g, 120 mmol), hydroxyethylstarch (30 g, average molecular weight: 429000, degree of substitution: 0.55), sodium gluconate (21.81 g, 100 mmol), potassium dihydrogen phosphate (0.885 g, 6.5 mmol) and dipotassium hydrogen phosphate (3.222 g, 18.5 mmol), and then distilled water was added thereto to a total amount of 1000 ml. This solution was immediately filtered and filled in a glass bottle. The bottle was tightly sealed and vapor-sterilized to give ET-Kyoto solution (hereinafter ET-K solution) having an osmotic pressure of 366 mOsm/l and pH of 7.35.

To the above-mentioned ET-K solution were added db-cAMP (manufactured by Daiichi Pharmaceutical Co., Ltd.), nitroglycerin (manufactured by Mitsubishi Pharma Corporation) and N-acetylcysteine to give New ET-Kyoto solution (hereinafter New ET-K solution).

Furthermore, to the above-mentioned ET-K solution was added db-cAMP (manufactured by Daiichi Pharmaceutical Co., Ltd.) to give modified New ET-Kyoto solution (hereinafter modified New ET-K solution).

The UW solution was purchased from Fujisawa Pharmaceutical Co., Ltd.

The compositions of the ET-K solution, New ET-K solution and modified New ET-K solution are as follows.

TABLE 1

| Component | ET-K | New ET-K | Modified New ET-K |
|---|---|---|---|
| α,α-Trehalose (mM) | 120 | 120 | 120 |
| Hydroxyethylstarch (g/l) | 30 | 29 | 30 |
| $Na^+$ (mM) | 100 | 107 | 100 |
| $K^+$ (mM) | 44 | 42 | 44 |
| $H_2PO_4^-$ or $HPO_4^{--}$ (mM) | 25 | 24 | 25 |
| Gluconic acid (mM) | 100 | 97 | 100 |
| db-cAMP (mM) | 0 | 2 | 2 |
| Nitroglycerin (mM) | 0 | 0.44 | 0 |
| N-Acetylcysteine (mM) | 0 | 10 | 0 |

(Experimental Group)

Group I: UW solution group (n=8), Group II: New ET-K solution group (n=6), Group III: modified New ET-K solution group (n=8). The liver was preserved under cooling in each preservation solution for 24 hr, and then syngeneic liver transplantation was performed. Rats were randomly assigned to each group.

(Transplantation Procedure)

In the UW group, the blood in the donor liver portal vein blood vessel was first replaced with 10 ml of Ringer's solution, and then the blood vessel was perfused with 10 ml of UW solution. In the New ET-K group and the modified New ET-K group, the blood in the donor liver portal vein blood vessel was directly replaced with 20 ml of each preservation solution. In all groups, the perfusion with the preservation solution was performed at a pressure of 15 $cmH_2O$. Then, liver grafts were preserved in respective preservation solutions at 4° C. for 24 hr. In the UW group, before transplantation, the inside of the portal vein blood vessel of the grafts was finally rinsed with 10 ml of Ringer's solution, whereby the UW solution was replaced. In the New ET-K group and the modified New ET-K group, the liver was implanted without the final rinsing. After preservation, a liver graft was orthotopically transplanted into a recipient rat. Both superior and inferior hepatic vena cavae were anastomosed with a surgical suture. The portal vein was connected by a semi-automatic anastomotic method using a polyethylene cuff (micro tube). In all transplantation operations, the anesthesia time was less than 14 minutes and the vena cave clamping time was less than 25 minutes.

(Postoperative Evaluation)

At 4 hours after the transplantation, the recipient rat subjected to the transplantation was re-anesthetized by intraperitoneal injection of ketamine. Bile was collected for 15 minutes to measure the bile output rate and bile contents. Blood samples were taken from inferior vena cave for measurements of serum ammonia, AST, ALT, LDH (all are most general evaluation indices for liver function) and hyaluronic acid (HA) (index for liver vascular endothelial cell function). Finally, graft was perfused via portal vein at a rate of 10 ml/min with 20 ml of Ringer's solution. Specimens for the transmission electron microscope (TEM) were perfused with 20 ml of 1.44% glutaraldehyde (GLA) solution. The rest was immersed in 10% formaldehyde and embedded in paraffin wax. Sections were subjected to routine hematoxylin eosin staining. TEM was performed for analysis of changes of the ultrastructures.

[2] Results (Survival Rate)

After transplantation of 24 hr-preserved liver grafts, the 7-day survival rate was 86% (7/8) in the modified New ET-K group and 25% (2/8) in the UW group. The survival rate was significantly better in the modified New ET-K group (Fisher's exact test: P<0.05; FIG. 1). In the New ET-K group, the 7-day survival rate was 0% (0/6), and the New ET-K solution failed to increase the 7 day survival rate.

From the above results, it has been clarified that the use of the modified New ET-K solution greatly enhances the survival rate after liver transplantation as compared to the use of the UW solution or the New ET-K solution. Moreover, it has been clarified that the survival rate after liver transplantation greatly increases by reducing the nitroglycerin content of the preservation solution, since the survival rate is extremely low when the New ET-K solution containing nitroglycerin is used.

(Serum Biochemistry)

Figure 2:
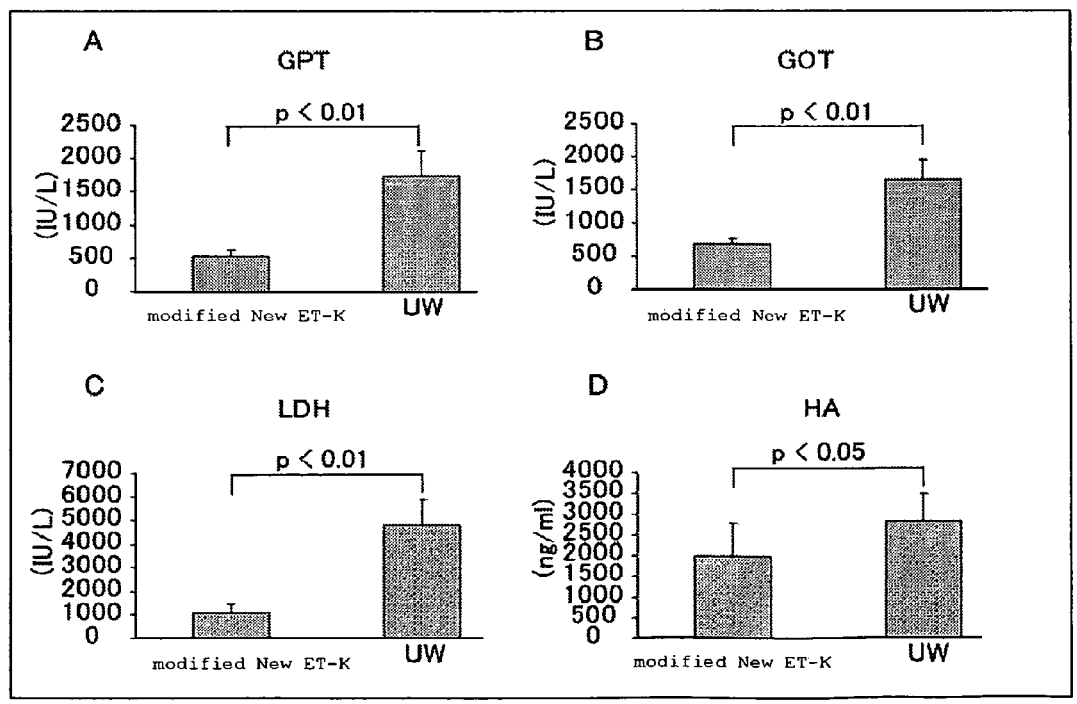
FIG. 2 is a graph showing the effect of a preservation solution on each serum biochemical marker reflecting hepatocyte injury or sinusoidal endothelial cell injury.

Serum AST (GOT), ALT (GPT), LDH and HA were measured at 4 hours after the transplantation. Hepatocyte injury, as assessed by ALT, AST and LDH levels, was significantly less in the modified New ET-K group than in the UW group (modified New ET-K/UW: ALT, 527±88/1728±380 IU/l, p<0.01; AST, 681±90/1652±292 IU/l, p<0.01; LDH, 1105±352/4796±1059 IU/l, p<0.01; FIGS. 2A, B and C). HA level reflected the injury of sinusoidal endothelial cell (SEC). HA levels were significantly lower in the modified New ET-K group as compared to the UW group (1988±791/2809±673 ng/ml, p<0.05; FIG. 2D).

From the above results, it has been clarified that the preservation effect of the modified New ET-K solution is superior in hepatocyte and sinusoidal endothelial cell, as compared to the UW solution.

(Blood Ammonia and Bile Production)

Figure 3:
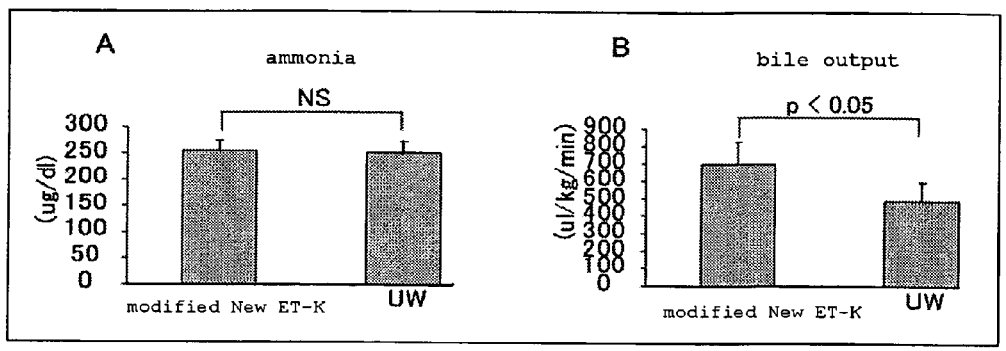
FIG. 3 is a graph showing the effect of a preservation solution on the liver function.

Ammonia and bile outputs were assessed as indices of the liver function. Although there was no significant difference in ammonia between the two groups at this time point (255±20/252±22 μg/dl, p>0.05; FIG. 3A), bile output was significantly higher in the modified New ET-K group (modified New ET-K/UW: 702±125/489±108 μl/kg/min, p<0.05; FIG. 3B).

From the above results, it has been clarified that the liver function maintaining effect of the modified New ET-K solution is high as compared to the UW solution.

(HE Staining)

Figure 4:
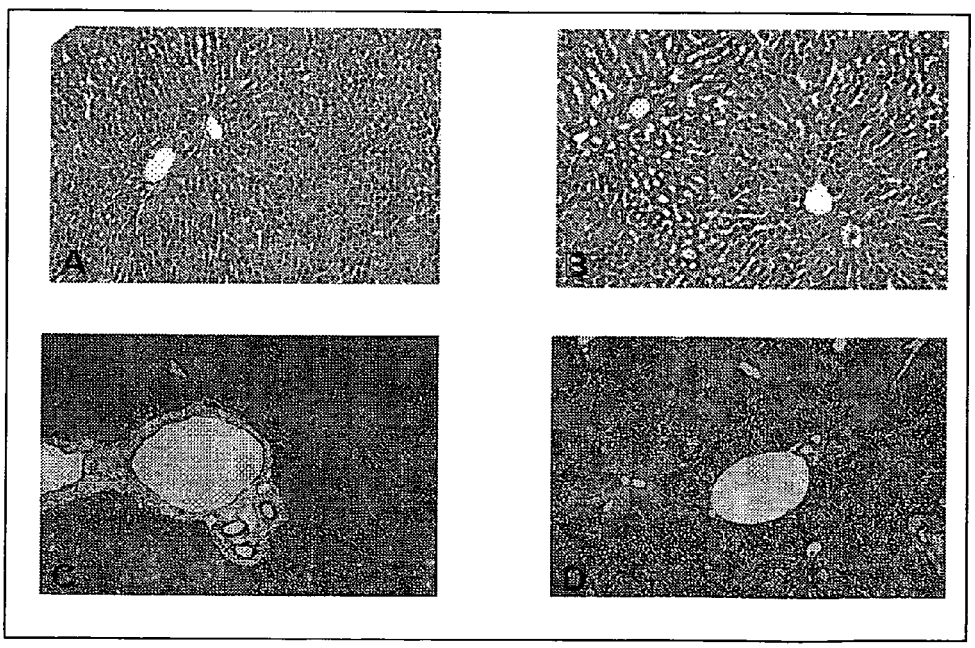
FIG. 4 is a photograph showing the effect of a preservation solution on histological changes in a liver graft. A and C: ET-Kyoto+db-cAMP, B and D: UW. A vs B: congestion of blood in sinusoid is marked in B than in A. C vs D: vacuolar denaturation is marked in D than in C and A.

Histologically, liver grafts preserved in the UW solution were more susceptible to reperfusion injury than those in the ET-K solution. There were less vacuolar denaturation, sinusoidal congestion and hemorrhage in the modified New ET-K group as compared to the UW group (FIG. 4).

From the above results, it has been clarified that the modified New ET-K solution more strongly protects the liver from reperfusion injury as compared to the UW solution.

(Electron Microscopic Findings)

Figure 5:
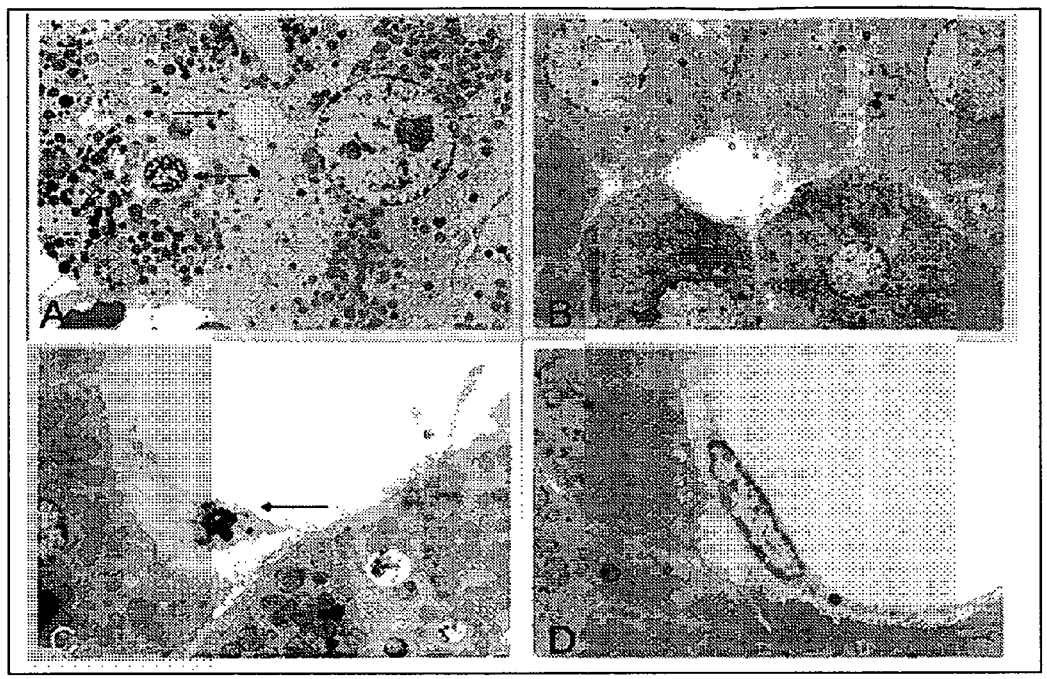
FIG. 5 is a photograph showing the effect of a preservation solution on the super structures of hepatocyte and sinusoidal endothelial cell. A and B: hepatocytes, C and D: sinusoidal endothelial cells, A and C: UW group, B and D: modified New ET-K group.

For further evaluation of morphological changes of SECs and hepatocytes, TEM was performed to analyze the ultrastructure of the 24-hour preserved liver grafts at 4 hours after transplantation. In the UW group, hepatocyte cell death, i.e., apoptotic changes (pyknosis, energy metabolism-related mitochondrial edema and vacuolar denaturation), was more frequently observed than in the modified New ET-K group (FIGS. 5A, B). Moreover, in the UW group, some SECs showed the features of apoptosis, such as detachment, discontinuity, bleb formation, nucleus condensation and apoptotic body (FIG. 5C). On the other hand, such kind of changes was mild in the modified New ET-K group, and SECs were often well preserved (FIG. 5D).

From the above results, it has been clarified that the modified New ET-K solution is superior in the action to maintain the ultrastructures of hepatocyte and SEC.

Example 2

[1] Materials and Method

In the same manner as in Example 1, syngenic liver transplantation was performed on 8-week-old inbred male Lewis rats (SLC), and the survival rate after transplantation of the liver preserved in preservation solutions containing various concentrations of nitroglycerin (NTG) was evaluated.

The preservation solutions used for the experiment were as follows:

ET-K+db-cAMP (2 mM)+1/4 NTG (0.11 mM)
ET-K+db-cAMP (2 mM)+1/8 NTG (0.055 mM)
ET-K+db-cAMP (2 mM)+1/100 NTG (0.0044 mM)
ET-K+db-cAMP (2 mM) (control: modified New ET-K solution)

The conditions for liver transplantation were the same as in Example 1 except that the kind of the preservation solution was different.

[2] Results

The results are shown in Table 2.

TABLE 2

| group | donor weight (g) | preservation period (min) | recipient weight (g) | liver-free period (min) | IVC reperfusion (min) | number of survived days |
|---|---|---|---|---|---|---|
| control | 368 | 1474 | 410 | 13 | 23 | 7 |
| control | 364 | 1434 | 376 | 16 | 28 | 1 |
| control | 340 | 1440 | 364 | 16 | 27 | 7 |
| 1/4 | 398 | 1500 | 410 | 15 | 26 | 1 |
| 1/4 | 356 | 1375 | 360 | 15 | 29 | 2 |
| 1/4 | 358 | 1398 | 366 | 16 | 30 | 1 |
| 1/8 | 396 | 1479 | 396 | 14 | 26 | 2 |
| 1/8 | 342 | 1378 | 352 | 16 | 27 | 2 |
| 1/8 | 328 | 1407 | 330 | 16 | 29 | 1 |
| 1/8 | 342 | 1438 | 370 | 16 | 27 | 1 |
| 1/100 | 338 | 1449 | 350 | 15 | 26 | 2 |
| 1/100 | 350 | 1443 | 380 | 15 | 26 | 7 |

The 7-day survival rate after liver transplantation was 66% (2/3) in the control (modified New ET-K) group. When the nitroglycerin content was reduced to 1/8-1/4 (0.055-0.11 mM) of that of the New ET-K solution, the 7-day survival rate was 0%, and it was therefore suggested that the toxicity due to nitroglycerin was not sufficiently reduced within this concentration range. On the other hand, when the nitroglycerin content was reduced to 1/100 (0.0044 mM) of that of the New ET-K solution, the 7-day survival rate was 50% (½), which was almost the same as that of the control group. Accordingly, it has been demonstrated that the toxicity due to nitroglycerin is hardly expressed when the nitroglycerin content is not more than 0.0044 mM, and the survival rate of the recipient after liver transplantation increases.

Example 3

[1] Materials and Method

In the same manner as in Example 1, syngenic liver transplantation was performed on 8-week-old inbred male Lewis rats (SLC), and whether or not an increase in the survival rate after liver transplantation due to the addition of db-cAMP to the ET-K solution can be observed in other preservation solutions was examined.

The preservation solutions used for the experiment were as follows:
ET-K
UW
ET-K+db-cAMP (2 mM) (modified New ET-K solution)
UW+db-cAMP (2 mM)

The conditions for liver transplantation were the same as in Example 1 except that the kind of the preservation solution was different.

[2] Results

Figure 6:
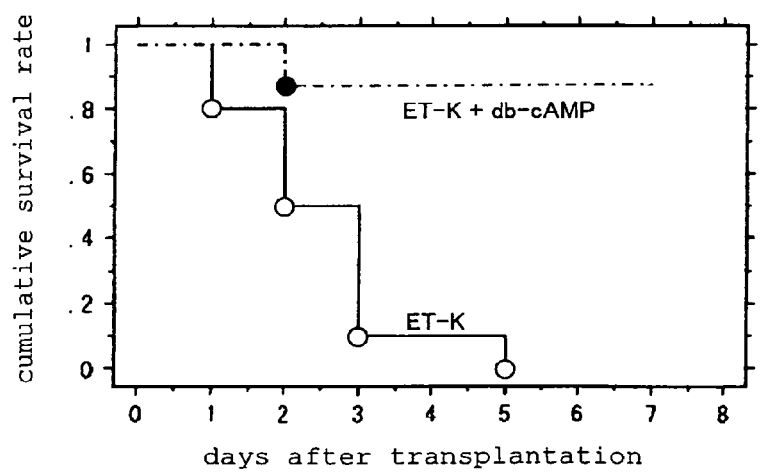
FIG. 6 is a graph showing the cumulative survival rate of rat transplanted with the liver preserved in ET-K solution or ET-K solution containing db-cAMP (Kaplan-Meier method). The solid line shows ET-K group, and the dotted line shows ET-K+db-cAMP group. A white circle shows development of ET-K group and a black circle shows development of ET-K+ db-cAMP group.

The 7-day survival rate after liver transplantation was 86% (7/8) in the ET-K+db-cAMP group, and 0% (0/10) in the ET-K group. Due to the addition of db-cAMP, the survival rate remarkably increased (FIG. 6).

Figure 7:
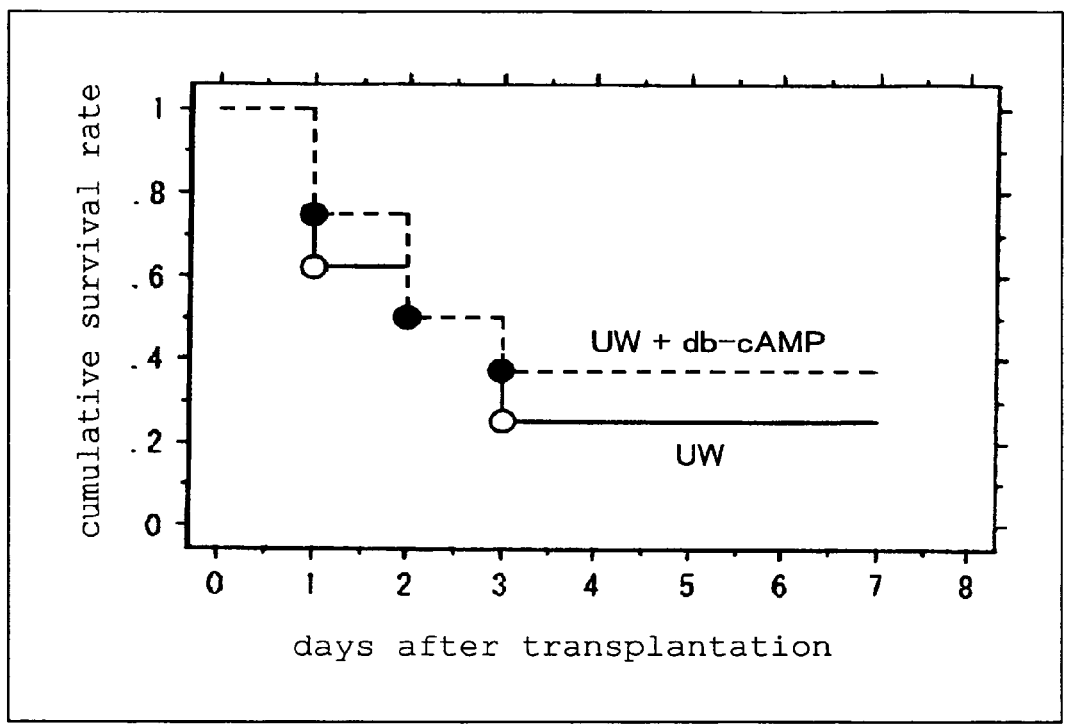
FIG. 7 is a graph showing the cumulative survival rate of rat transplanted with the liver preserved in UW solution or UW solution containing db-cAMP (Kaplan-Meier method). The solid line shows UW group, and the dotted line shows UW+db-cAMP group. A white circle shows development of UW group and a black circle shows development of UW+db-cAMP group.

On the other hand, the rate was 38% (3/8) in the UW+db-cAMP group, and 25% (2/8) in the UW group. The survival rate slightly increased due to the addition of db-cAMP, but a remarkable effect as that observed using the ET-K solution was not found (FIG. 7).

Accordingly, it has been suggested that the remarkable increase in the post-transplant survival rate due to the addition of db-cAMP is an effect specific to the ET-K solution.

Moreover, since the superior organ preservation effect of the ET-K solution containing db-cAMP has been confirmed in the liver as well as the kidney, it has been suggested that the above-mentioned preservation solution of the present invention is also useful for the preservation of kidney.

Industrial Applicability

The liver preservation solution of the present invention has superior liver preservation capability, and is useful in the field of transplantation medicine.

This application is based on a patent application No. 2005-299314 filed in Japan (filing date: Oct. 13, 2005), the contents of which are incorporated in full herein by this reference.

The invention claimed is:

1. A method of preserving liver, which comprises preserving an isolated liver in a tissue preservation solution comprising at least the following components within the following ranges and having a nitroglycerin content of not more than 0.0044 mM:

| | |
|---|---|
| dibutyryl cAMP | 1.5-3 mM |
| trehalose | 110-130 mM |
| hydroxyethylstarch | 25-35 g/l |
| $Na^+$ | 90-110 mM |
| $K^+$ | 40-50 mM |
| $H_2PO_4^-$ or $HPO_4^{--}$ | 20-30 mM |
| at least one kind selected from $Cl^-$, $HCO_3^-$, $CO_3^{--}$, organic acid and organic acid anion | 90-110 mM. |

2. The method of claim 1, wherein the tissue preservation solution is substantially free of nitroglycerin.

\* \* \* \* \*